United States Patent
Betz et al.

(10) Patent No.: US 8,246,680 B2
(45) Date of Patent: Aug. 21, 2012

(54) PATIENT-SPECIFIC SPINAL IMPLANTS AND RELATED SYSTEMS AND METHODS

(75) Inventors: Randal Betz, Ocean City, NJ (US); Guilhem Denoziere, Atlanta, GA (US)

(73) Assignee: SpineMedica, LLC, Marietta, GA (US)

( * ) Notice: Subject to any disclaimer, the term of this patent is extended or adjusted under 35 U.S.C. 154(b) by 1488 days.

(21) Appl. No.: 11/753,755

(22) Filed: May 25, 2007

(65) Prior Publication Data
US 2007/0276501 A1    Nov. 29, 2007

Related U.S. Application Data

(60) Provisional application No. 60/803,141, filed on May 25, 2006.

(51) Int. Cl.
*A61F 2/44* (2006.01)
(52) U.S. Cl. .................... 623/17.11; 606/130
(58) Field of Classification Search .......... 606/130; 623/17.14–17, 15, 17.11; 600/425, 594
See application file for complete search history.

(56) References Cited

U.S. PATENT DOCUMENTS

| | | | |
|---|---|---|---|
| 4,759,766 A | 7/1988 | Büttner-Janz et al. | |
| 4,911,718 A * | 3/1990 | Lee et al. | 623/17.15 |
| 5,314,477 A | 5/1994 | Marnay | |
| 5,401,269 A | 3/1995 | Büttner-Janz et al. | |
| 5,514,180 A | 5/1996 | Heggeness et al. | |
| 5,556,431 A | 9/1996 | Büttner-Janz | |
| 5,981,826 A | 11/1999 | Ku et al. | |
| 6,231,605 B1 | 5/2001 | Ku | |
| 6,786,930 B2 * | 9/2004 | Biscup | 623/16.11 |
| 2005/0055099 A1 | 3/2005 | Ku | |
| 2006/0282020 A1 * | 12/2006 | Bertagnoli et al. | 600/594 |

FOREIGN PATENT DOCUMENTS

WO    WO 03/059211    7/2003

OTHER PUBLICATIONS

International Search Report and Written Opinion for International Application No. PCT/US2007/012517 mailed Mar. 10, 2008 (20 pages).
Stauffer et al. "Poly(vinyl alcohol) hydrogels prepared by freezing—thawing cyclic processing" *Polymer* 33:3932-2936 (1992).

* cited by examiner

*Primary Examiner* — Eduardo C Robert
*Assistant Examiner* — Tara Carter
(74) *Attorney, Agent, or Firm* — Myers Bigel Sibley & Sajovec, P.A.

(57) ABSTRACT

Methods and systems for generating custom implants by programmatically analyzing a patient's image data to electronically obtain shapes and dimensions of relevant anatomical features of a target region of the patient; and fabricating a patient-specific replacement implant for the patient using the analyzed patient image data. Related patient-specific spinal implants are also described.

18 Claims, 13 Drawing Sheets

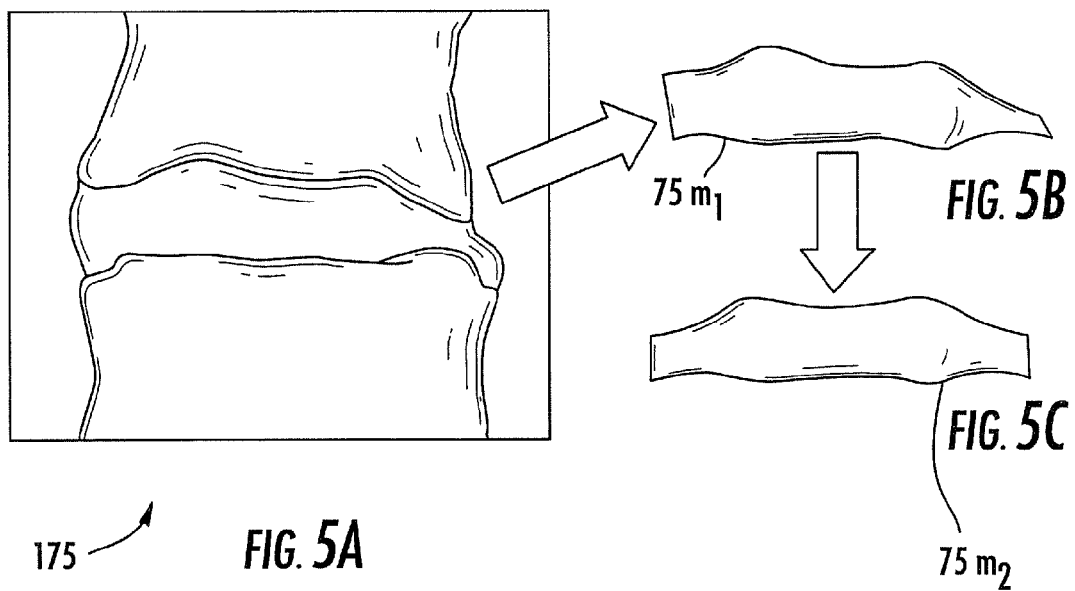

MOLDING

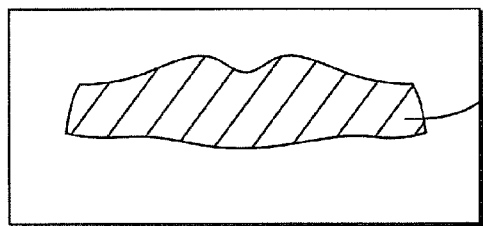
FIG. 12A
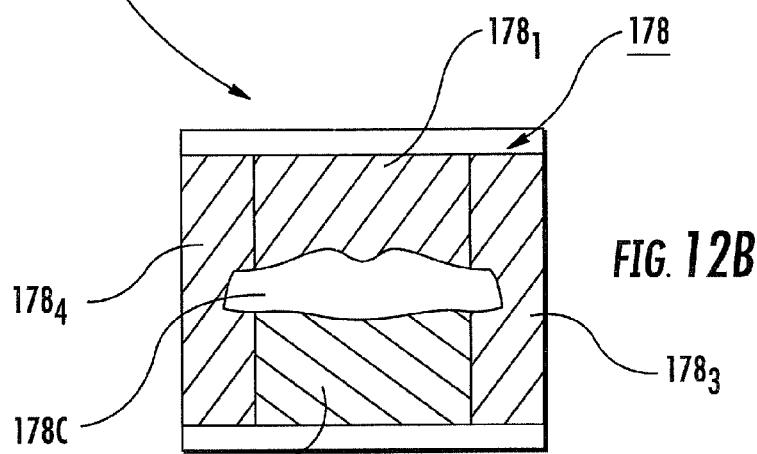
FIG. 12B
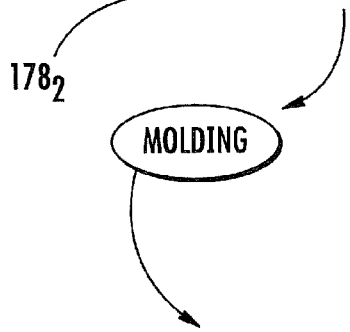
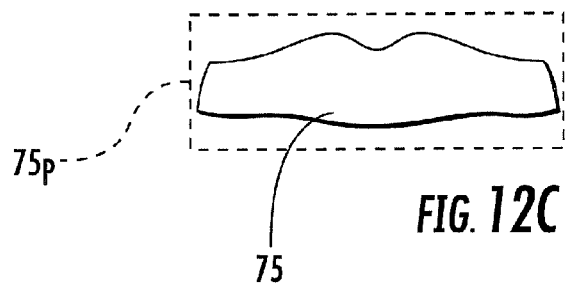
FIG. 12C

PATIENT-SPECIFIC SPINAL IMPLANTS AND RELATED SYSTEMS AND METHODS

RELATED APPLICATIONS

This application claims priority to U.S. Provisional Application Ser. No. 60/803,141, filed May 25, 2006, the entire contents of the above-referenced document is hereby incorporated herein by reference as if recited in full herein.

FIELD OF THE INVENTION

The invention relates to implants, and may be particularly relevant to spinal implants.

BACKGROUND OF THE INVENTION

The vertebrate spine is made of bony structures called vertebral bodies that are separated by relatively soft tissue structures called intervertebral discs. The intervertebral disc is commonly referred to as a spinal disc. The spinal disc primarily serves as a mechanical cushion between the vertebral bones, permitting controlled motions between vertebral segments of the axial skeleton. The disc acts as a joint and allows physiologic degrees of flexion, extension, lateral bending, and axial rotation. The disc must have sufficient flexibility to allow these motions and have sufficient mechanical properties to resist the external forces and torsional moments caused by the vertebral bones.

The normal disc is a mixed avascular structure having two vertebral end plates ("end plates"), an annulus fibrosis ("annulus") and a nucleus pulposus ("nucleus"). Typically, about 30-50% of the cross sectional area of the disc corresponds to the nucleus. Generally described, the end plates are composed of thin cartilage overlying a thin layer of hard, cortical bone that attaches to the spongy cancellous bone of the vertebral body. The end plates act to attach adjacent vertebrae to the disc.

The annulus of the disc is a relatively tough, outer fibrous ring. For certain discs, particularly for discs at lower lumbar levels, the annulus can be about 10 to 15 millimeters in height and about 10 to 15 millimeters in thickness, recognizing that cervical discs are smaller.

Inside the annulus is a gel-like nucleus with high water content. The nucleus acts as a liquid to equalize pressures within the annulus, transmitting the compressive force on the disc into tensile force on the fibers of the annulus. Together, the annulus and nucleus support the spine by flexing with forces produced by the adjacent vertebral bodies during bending, lifting, etc.

The compressive load on the disc changes with posture. When the human body is supine, the compressive load on the third lumbar disc can be, for example, about 200 Newtons (N), which can rise rather dramatically (for example, to about 800 N) when an upright stance is assumed. The noted load values may vary in different medical references, typically by about ±100 to 200 N. The compressive load may increase, yet again, for example, to about 1200 N, when the body is bent forward by only 20 degrees.

The spinal disc may be displaced or damaged due to trauma or a degenerative process. A disc herniation occurs when the annulus fibers are weakened or torn and the inner material of the nucleus becomes permanently bulged, distended, or extruded out of its normal, internal annular confines. The mass of a herniated or "slipped" nucleus tissue can compress a spinal nerve, resulting in leg pain, loss of muscle strength and control, and even paralysis. Alternatively, with discal degeneration, the nucleus loses its water binding ability and deflates with subsequent loss in disc height. Subsequently, the volume of the nucleus decreases, causing the annulus to buckle in areas where the laminated plies are loosely bonded. As these overlapping plies of the annulus buckle and separate, either circumferential or radial annular tears may occur, potentially resulting in persistent and disabling back pain. Adjacent, ancillary facet joints will also be forced into an overriding position, which may cause additional back pain. The most frequent site of occurrence of a herniated disc is in the lower lumbar region. The cervical spinal disks are also commonly affected.

There are several types of treatment currently being used for treating herniated or degenerated discs: conservative care, discectomy, nucleus replacement, fusion and prosthesis total disc replacement (TDR). It is believed that many patients with lower back pain will get better with conservative treatment of bed rest. For others, more aggressive treatments may be desirable.

Disectomy can provide good short-term results. However, a discectomy is typically not desirable from a long-term biomechanical point of view. Whenever the disc is herniated or removed by surgery, the disc space will narrow and may lose much of its normal stability. The disc height loss may cause osteo-arthritis changes in the facet joints and/or compression of nerve roots over time. The normal flexibility of the joint is lost, creating higher stresses in adjacent discs. At times, it may be necessary to restore normal disc height after the damaged disc has collapsed.

Fusion is a treatment by which two vertebral bodies are fixed to each other by a scaffold. The scaffold may be a rigid piece of metal, often including screws and plates, or allo or auto grafts. Current treatment is to maintain disc space by placement of rigid metal devices and bone chips that fuse two vertebral bodies. The devices are similar to mending plates with screws to fix one vertebral body to another one. Alternatively, hollow metal cylinders filled with bone chips can be placed in the intervertebral space to fuse the vertebral bodies together (e.g., LT-Cage™ from Sofamor-Danek or Lumbar I/F CAGE™ from DePuy). These devices have disadvantages to the patient in that the bones are fused into a rigid mass with limited, if any, flexible shock absorption that would normally occur with a natural spinal disc. Fusion may generally eliminate symptoms of pain and stabilize the joint. However, because the fused segment is fixed, the range of motion and forces on the adjoining vertebral discs can be increased, possibly enhancing their degenerative processes.

Some recent TDR devices have attempted to allow for motion between the vertebral bodies through articulating implants that allow some relative slippage between parts (e.g., ProDisc®, Charite™). See, e.g., U.S. Pat. Nos. 5,314,477, 4,759,766, 5,401,269 and 5,556,431. As an alternative to the metallic-plate, multi-component TDR (total disc replacement) designs, a flexible solid elastomeric spinal disc implant that is configured to simulate natural disc action (i.e., can provide shock absorption and elastic tensile and compressive deformation) is described in U.S. Patent Application Publication No. 2005/0055099 to Ku, the contents of which are hereby incorporated by reference as if recited in full herein.

Other parts of the spine may also deteriorate and/or need repair and implants for various portions of the spine may be desirable.

Unfortunately, conventionally, a patient's local bone structure may be rather severely surgically altered, contoured and/or exercised to accept the shape and size of the conventional disc implant, which may induce stress concentration and/or undesirable damage to bony structures.

SUMMARY OF EMBODIMENTS OF THE INVENTION

Embodiments of the invention are directed to providing patient-specific implants that can be custom configured to fit a target space or structure in a patient and/or formed based on patient image data and input from a clinician to customize treatment and/or provide ease of implantation in the patient.

Embodiments of the invention are directed to methods for generating custom arthoplasty implants, including spinal implants. The methods include: (a) programmatically analyzing a patient's image data to electronically obtain shapes and dimensions of relevant anatomical features of a target region of the patient; and (b) fabricating a patient-specific replacement implant for the patient using the analyzed patient image data.

In particular embodiments, the implant can be a spinal implant, such as a total disc replacement (TDR), a nucleus, a facet joint or an inter-process spacer and the like.

In some embodiments, wherein the spinal implant comprises a TDR, the method can further include, before the fabricating step, electronically generating a 3-D model of at least one level of a target disc space of each patient using respective patient image data, then generating a 3-D model of the total disc replacement spinal implant based on data from the 3-D model of the target disc space.

In some embodiments, the programmatically analyzing step can include generating an electronic graphic 3-D anatomical model of at least one target spinal location undergoing treatment; and electronically constructing the patient-specific replacement spinal implant based on the generated model.

In some embodiments, the patient-specific spinal implant is an intervertebral disc implant, and the programmatically analyzing step includes: (a) generating an electronic graphic anatomical model of at least one target region or space (such as, for example, an intervertebral disc space) undergoing treatment; (b) electronically constructing a replacement implant model based on the target space model; and (c) electronically correcting the constructed model according to the patient's pathology and/or anatomy to shape and/or size the patient-specific replacement implant.

In some embodiments, the implant comprises a TDR implant and the methods can include: electronically determining 3-D surface contours of vertebral endplates at the at least one target disc level to be treated using the patient image data; and generating an electronic 3-D model of the total disc replacement implant that includes the 3-D surface contours that substantially corresponds to the determined 3-D contours.

Other embodiments are directed to systems for producing custom implants. The systems include a processor system configured to generate a 3-D graphic model of a patient-specific implant using dimensions and features of a target region of a respective patient obtained from patient medical image data.

In some embodiments, the systems can include at least one clinician workstation in communication with the processor system. The workstation can include a display configured to display the 3-D model of the implant (which may be, for example, a spinal implant). The systems may also include: a 3-D model construct circuit in communication with the workstation configured to generate the 3-D model of the patient-specific implant and to generate a 3-D model of a target actual space in respective patients. The systems may also include a patient image data server in communication with the 3-D model construct circuit.

Still other embodiments are directed to methods for generating custom spinal implants that include: (a) programmatically generating an electronic graphic anatomical model of at least one target intervertebral disc space undergoing treatment using electronic patient image data to define shapes and dimensions of relevant anatomical features of a spine of the patient; (b) electronically constructing a replacement implant model based on the anatomical disc space model; and (c) electronically correcting the constructed model according to the patient's pathology and/or anatomy to shape and/or size the patient-specific total disc replacement implant.

Other embodiments are directed to medical implants. The implants can include an arthoplastic implant, such as, for example, a total disc replacement (TDR) spinal implant comprising superior and inferior surfaces customized to match local bone structure in a respective patient. The TDR or other arthoplastic implant may optionally include a flexible molded elastomeric implant having a predetermined patient-specific shape and dimensions.

Some embodiments are directed to at least one medical arthoplasty implant in a sterile package, the implant in the package comprising a body with a shape and dimensions customized to match local bone structure in a target joint space of a respective patient.

Some embodiments are directed to computer program products for providing physician interactive access to patient medical volume data for constructing spinal implants using a computer network. The computer program product includes a computer readable storage medium having computer readable program code embodied in the medium. The computer-readable program code includes: (a) computer readable program code configured to generate patient-specific graphic 3-D spinal implant models using data from medical images of a target region of a patient; and (b) computer readable program code configured to interactively accept user input to adjust features, sizes and/or dimensions of the patient-specific spinal implant models.

In some embodiments, a display can display a virtual image of an implant shape that can be placed in the target space and altered in different shapes and dimensions to allow a clinician to virtually visualize the implant's affect post-surgery.

It is noted that any of the features claimed with respect to one type of claim, such as a system, apparatus, or computer program, may be claimed or carried out as any of the other types of claimed operations or features.

Further features, advantages and details of the present invention will be appreciated by those of ordinary skill in the art from a reading of the figures and the detailed description of the embodiments that follow, such description being merely illustrative of the present invention.

BRIEF DESCRIPTION OF THE DRAWINGS

FIG. 5A is a 2-D screen shot of a patient image of a spinal disc space targeted for treatment.

FIG. 5B is an electronic model of a natural spinal disc constructed to have substantially the same dimensions and shape as the spinal disc in the image of FIG. 5A.

FIG. 5C is an electronic model of spinal implant adjusted to correct a scoliotic angle relative to the natural disc model shown in FIG. 5B according to embodiments of the present invention.

FIGS. 12A-12C are schematic illustrations of exemplary operations that can be used to mold patient specific implants according to embodiments of the present invention.

DETAILED DESCRIPTION

Figure 1A:
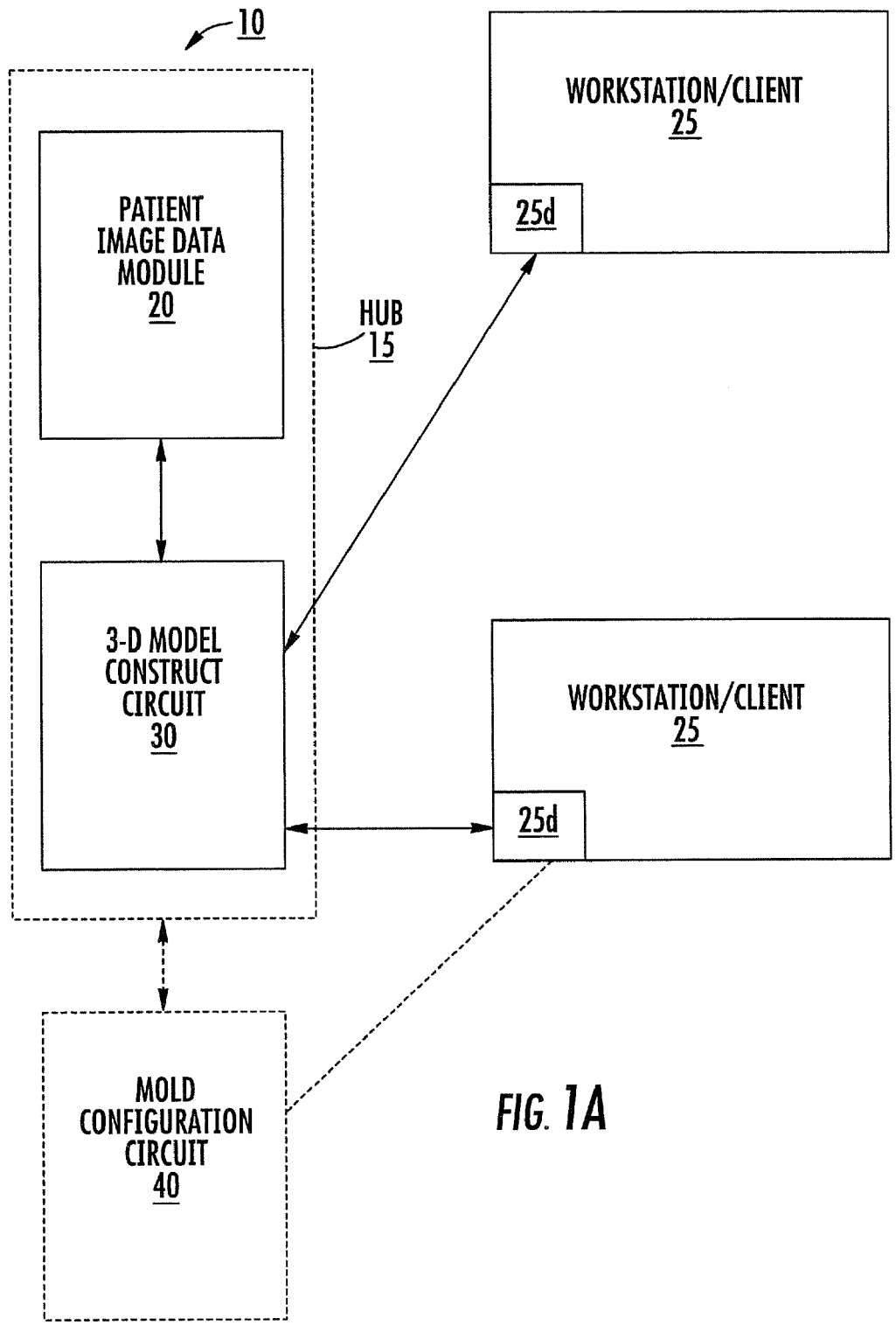
FIG. 1A is a schematic illustration of a system configured to provide data used to generate patient-specific implants according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

As will be appreciated by one of skill in the art, embodiments of the invention may be embodied as a method, system, data processing system, or computer program product. Accordingly, the present invention may take the form of an entirely software embodiment or an embodiment combining software and hardware aspects, all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic or other electronic storage devices.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise. The term "programmatically" means under the direction of computer or processor implemented programs (program code).

The term "automatic" means that substantially all or all of the operations so described can be carried out without requiring the assistance and/or manual input of a human operator. The term "electronic" means that the system, operation or device can be carried out using any suitable electronic media and typically includes programmatically controlling communication between a server in communication with a patient image database and workstations using a computer network. The term "hub" means a node and/or control site (or sites) that controls data exchange using a computer network.

Although described primarily herein with respect to spinal implants, embodiments of the invention are also directed to any implant, typically arthoplasty (joint replacement or joint treatment) implants for any joint in an animal body, typically a human body. The terms "spinal disc implant" and "spinal disc prosthesis" are used interchangeably herein to designate total disc replacements using an implantable total disc replacement (TDR) prosthesis (rather than a nucleus only) and as such are configured to replace the natural spinal disc of a mammalian subject (for veterinary or medical (human) applications). In contrast, the term "spinal implant" includes TDR spinal disc implants and alternative spinal implants, such as, for example, spinal annulus implants, spinal nucleus implants, facet (facet joint replacement) implants, posterior dynamic stabilization implants (such as inter-process spacers), and spinous process implants as well as implants for other portions of the spine.

The term "match" means to take on a shape that corresponds to target local (bone) structure interfaces. For example, for a replacement intervertebral disc, the superior and/or inferior surfaces can be fabricated to have local depressions and rises that mimic that of the excisable natural bone in a manner that engages and accepts the irregularities of adjacent local bone to provide a more natural stable position and/or that can provide increased contact area between the implant and adjacent bone structure t to improve load distribution and increase durability of the device and the bone over standardized surfaces of conventional devices.

The term "keel" means an implant component, feature or member that is configured to be received in a recess or mortise in an adjacent bone to facilitate short and/or long-term fixation and/or to provide twist or torsion resistance in situ. The term "flexible" used with respect to the keel means that the member could be flexed or bent. In some embodiments, the implant can include a keel, which may be flexible but has sufficient rigidity to be substantially self-supporting so as to be able to substantially maintain a desired configuration outside of the body. If flexible, the keel can include reinforcement to increase its rigidity. The term "flexible" with respect to a total disc replacement implant means that the implant is resilient as will be discussed further below. See, e.g., U.S. Patent Application Publication No. 2005/0055099 to Ku, the contents of which are hereby incorporated herein by reference thereto.

The term "mesh" means any flexible material in any form including, for example, knotted, braided, extruded, stamped, knitted, woven or otherwise, and may include a material with a substantially regular foramination pattern and/or irregular foramination patterns.

The term "macropores" refers to apertures having at least about a 1 mm diameter or width size, typically a diameter or width that is between about 1 mm to about 3 mm, and more typically a diameter or width that is between about 1 mm to about 1.5 mm (the width dimension referring to non-circular apertures). The macropores may promote bony through-growth for increased fixation and/or stabilization over time.

The present invention may be embodied as devices, systems, methods, and/or computer program products. Accordingly, the present invention may be embodied in hardware and/or in software (including firmware, resident software, micro-code, etc.). Furthermore, the present invention may take the form of a computer program product on a computer-usable or computer-readable storage medium having computer-usable or computer-readable program code embodied in the medium for use by or in connection with an instruction execution system. In the context of this document, a computer-usable or computer-readable medium may be any medium that can contain, store, communicate, propagate, or transport the program for use by or in connection with the instruction execution system, apparatus, or device.

The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM). Note that the computer-usable or computer-readable medium could even be paper or another suitable medium, upon which the program is printed, as the program can be electronically captured, via, for instance, optical scanning of the paper or other medium, then compiled, interpreted, or otherwise processed in a suitable manner, if necessary, and then stored in a computer memory.

Computer program code for carrying out operations of the present invention may be written in an object oriented programming language such as Java, Smalltalk or C++. However, the computer program code for carrying out operations of the present invention may also be written in conventional procedural programming languages, such as the "C" programming language or in a visually oriented programming environment, such as VisualBasic.

Certain of the program code may execute entirely on one or more of the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider). As will be discussed further below, typically, some program code executes on a workstation "client" computer and some program code executes on a hub server (such as a Patient Image Data Server and/or a web application or Administrative Server) with communication between the clients and the hub server using a computer network, for example, the Internet.

The invention is described in part below with reference to flowchart illustrations and/or block diagrams of methods, systems, computer program products and data and/or system architecture structures according to embodiments of the invention. It will be understood that each block of the illustrations, and/or combinations of blocks, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory or storage that can direct a computer or other programmable data processing apparatus to function in a particular manner, such that the instructions stored in the computer-readable memory or storage produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

Referring to FIG. 1A, a system 10 for facilitating patient-specific (or custom) spinal implants is shown. In some embodiments, the system 10 can be implemented using a computer network and can include at least one processor or processor system that can be used to analyze and/or extract geometric and dimensional data from patient image data. The processor can be a digital signal processor. The term "computer network" includes one or more local area networks (LAN), wide area networks (WAN) and may, in certain embodiments, include a private intranet and/or the public Internet (also known as the World Wide Web or "the web"). The system 10 can operate on one or more computers, with a Patient Image Data Module 20 and workstations 25. Where computer networks are used, the workstations may be considered "clients" and the Patient Image Module 20 may reside on a Patient Image Server, such as, for example, a hub 15 that is in communication with the client workstations 25.

The workstations 25 typically include at least one display 25d that can be used to view images such as the 3-D model of the natural deteriorated, injured target structure and/or a 3-D model of the artificial implant. The hub 15 and/or workstation(s) 25 can also be in communication with a 3-D model construct circuit 30 and, optionally, a mold configuration circuit 40. The 3-D model construct circuit 30 can be configured to generate a patient-specific 3-D model of a spinal implant using patient image data. The mold configuration circuit 40 can be used to define a mold body that can create a molded implant having the defined patient-specific shape.

At least one client workstation 25 can reside at a clinician facility, such as a clinic or medical facility or physician's office, and another may reside at a site remote from the clinician facility, such as at an implant pre-manufacturing or manufacturing site or custom-shape construct site. The hub 15 can be a single server or computer and may reside at a central (administrative) site or can comprise a plurality of servers or computers that electronically communicate with hardware and/or software residing at different sites (nodes).

Figure 1B:
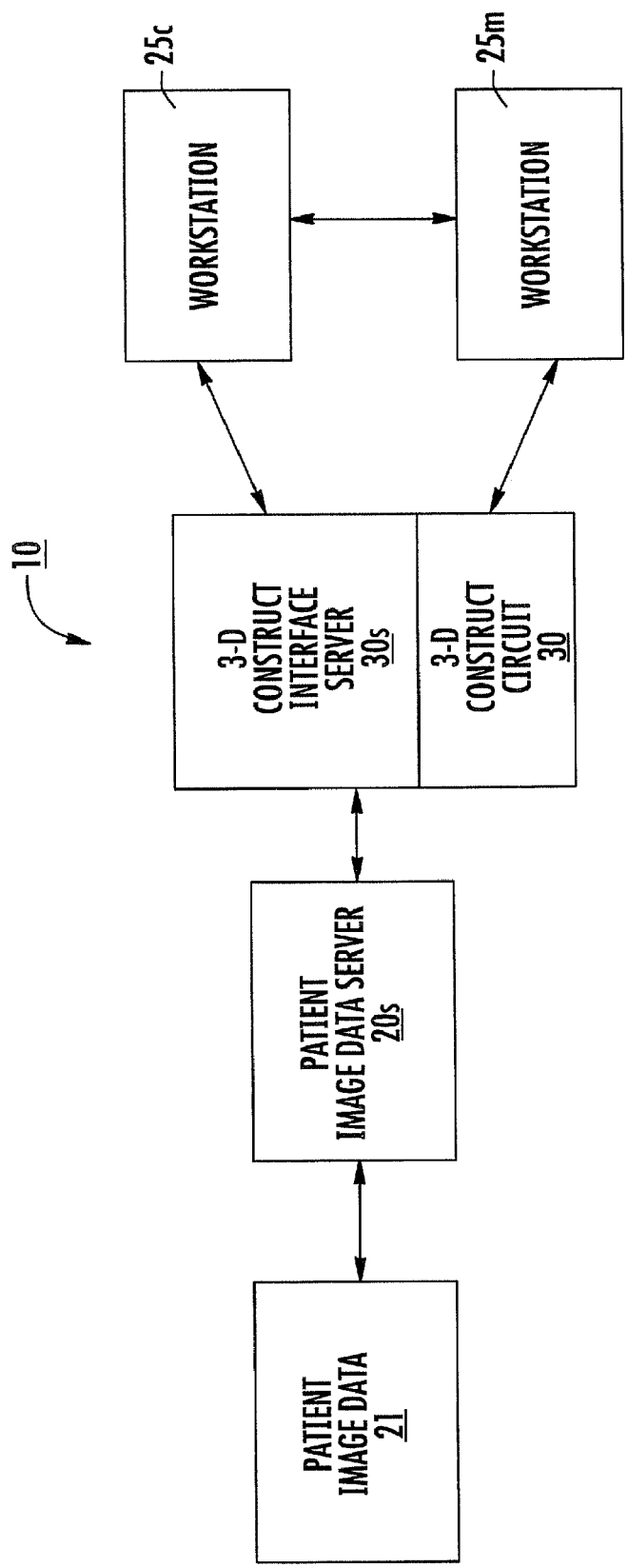
FIG. 1B is a schematic illustration of a system configured to provide data used to generate patient-specific implants according to embodiments of the present invention.

As shown in FIG. 1B, the 3-D model construct circuit 30 can reside in or be controlled by a 3-D construct interface server 30s that retrieves patient image data 21 and relays to the requesting workstation 25. The patient image data 21 may reside on the server 20s or may reside in a different server or other electronic storage device and communicate with the patient image data server 20s or directly with the interface server 30s and/or circuit 30. Typically, the custom or patient-specific implant will have a 3-D shape. Volumetric image data that can be analyzed to obtain shapes and dimensions for the implant can be generated from known imaging modalities, such as, for example, MRI (Magnetic Resonance Imaging) and CT (Computed Tomography). Known two-dimensional (2-D) and three-dimensional (3-D) visualization products provide medical images that can render images from stored electronic data files. The data input used to create the image renderings can be a stack of image slices from a desired imaging modality, for example, a CT and/or MRI modality. The visualization can convert the image data into an image volume to create renderings that can be displayed on a workstation display. Image visualizations using the multi-dimensional image data can be carried out using any suitable system such as, for example, PACS (Picture Archiving and Communication System). PACS is a system that receives images from the imaging modalities, stores the data in archives, and distributes the data to radiologists and clinicians for viewing (and can refer to sub portions of these systems). Thus, the 3-D model construct circuit 30 can be configured to construct a spinal implant shape and size based on patient image data of a target treatment region (such as a disc space) in the patient.

In some embodiments, some workstations 25 may also be configured to communicate with other workstations via a portal or other interface system. That is, a first clinician may forward a request for construction of a custom spinal implant for Patient A to a second clinician (that may be an implant design or other specialist) that may be onsite or remote for a virtual "consult". In some embodiments, the system 10 can be configured to generate an initial implant shape, then allow clinician interactive input for adjusting shapes, features, and/or dimensions, as will be discussed further below. The system 10 can access the patient image data and electronically generate a patient-specific implant construct model.

In other embodiments, imaging information obtained in advance of a surgical procedure can be carried out to evaluate the target implant space and determine the associated shapes and dimensions for a particular patient, including, for example, width space, wedge angle, anterior height, concavity of anterior and superior surfaces, and the like. This information can be used to select which of certain pre-fabricated implant sizes (S, M, L, XL), and which wedge angle (convexity that matches the concavity of the target disc) within that size (6, 10 or 14 degrees) as well as which anterior height (9, 11 or 13 mm) is desired. The wedge angle and anterior heights are examples, and may be suitable for typical L4 or L5 replacements. In addition, the same information can be used to select which trial size with its different convexities, and anterior heights and the like should be provided in the surgical kit (the term "trial" refers to a surgical instrument for inserting into the target space before the implant itself to stabilize and/hold the space while inserting/drilling or milling a mortise or keel way). Unlike conventional implantation techniques, which allows a surgeon to select and try different implant sizes and/or shapes at the time of implantation for "correctness in feel", embodiments of the invention can directly provide the implants that matches patient physiology (patient matched implant or PMI) and reduces the time and labor associated with onsite selection of tools and implants on the day of surgery or during a surgical procedure and can provide a better fit for the respective patient.

In some embodiments, the patient-custom device can also have a custom formulation (e.g., stiffness, hardness, mobility, flexibility, compression or tensile strength and/or torsional strength), and/or also a custom variable formulation (softer or more compliant in some given regions relative to others) in order to better comply with the bone density/strength of the patient at the interface with the device. For example, patients with osteoporosis may benefit from devices that are softer or more flexible at the interface with the bone to allow for improved stress distribution and reduced risks of bone damage/collapse. Patients with a local bone defect and/or osteolysis may also benefit from a locally softer device (at the interface where the bone is weak) with increased hardness where the bone is stronger and can take a greater load. The patient-device can also be configured to allow for increased mobility in one direction relative to another, typically considering the status of local surrounding tissues and/or bone loading. Thus, in some embodiments, the custom device can be configured with custom position, size and shapes and the relative position of contacting elements (by its geometry), and can be designed to provide selectability of the formulation and mechanical properties of the material. This adjustability can allow significant therapeutic indications of such device.

In some embodiments, when a clinician finalizes or approves of a customized spinal implant configuration for a particular patient at a first location 25c (such as a medical facility), he/she can forward an electronic order or requisition with the specific implant shape or electronic data sufficient to generate the implant shape as defined by an electronic 3-D model of the implant to a workstation 25m associated with a manufacturing system, using HIPAA compliant data sharing. The term "HIPAA" refers to the United States laws defined by the Health Insurance Portability and Accountability Act. The requisition can be carried out electronically to schedule production in a "just in time" inventory system and can be made without using patient identifiable data, but using a system that correlates the specific implant shape to a patient and identifies the need date, and shipping information.

Figure 2:
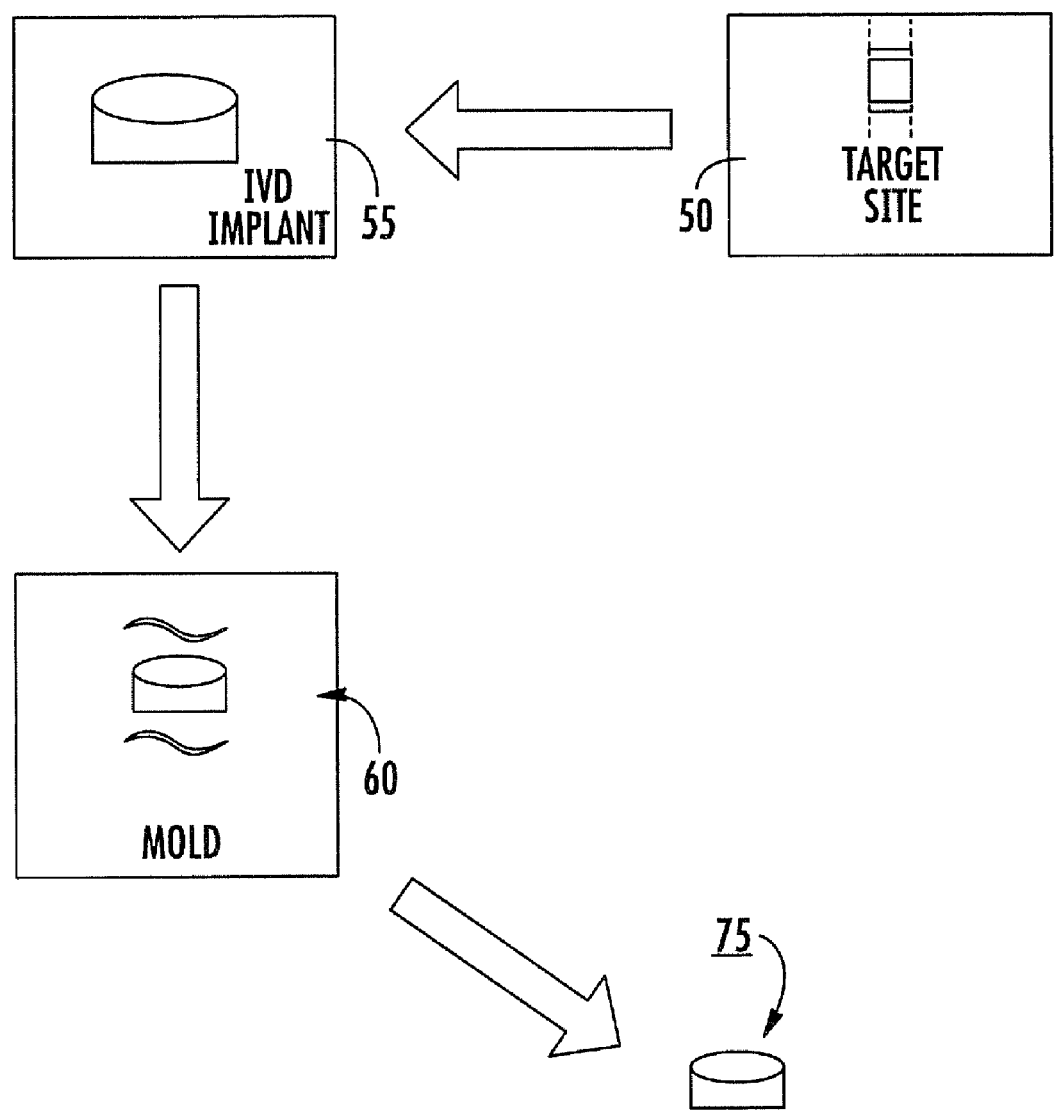
FIG. 2 is a schematic illustration of a serial sequence of steps that can be used to generate patient-specific spinal implants according to embodiments of the present invention.

FIG. 2 illustrates an exemplary sequence of actions that can be carried out to generate a patient-specific custom implant. In this example, a total disc replacement (TDR) is contemplated for this patient. As shown in FIG. 2, with screen 50, patient image data of at least the level of the lumbar spine with the affected disc space is electronically analyzed to generate a 3-D model of the target disc space. The 3-D model of the natural disc is generated using dimensions and geometric shapes of the natural disc and disc space based on the patient image data. An intervertebral (IVD) implant can be generated based on the model of the natural disc as shown in FIG. 2 at screen 55. Then, as shown by screen 60, in some embodiments, a patient-specific mold can be created by a CAD software system in response to the patient-specific IVD implant shape. The IVD implant 75 can be molded using the defined mold shape. Although shown as being molded, the implants can be custom fabricated using other manufacturing processes to yield implants with a geometry, features and/or size that is based on actual patient image data that defines each patient's specific anatomical space, injured target excisable bone structure and/or therapeutic goals.

In other embodiments, portions of an implant, such as, but not limited to, end plate surfaces, can be molded rather than the entire primary implant body. Also, as noted above, the spinal implant can be a nucleus or annulus implant, rather than a TDR implant or other spinal implants, such as a spinal facet joint replacements and spinous process inter-spacers or surface coverings for dynamic stabilization.

Additional features can be added to the implant after molding for fixation or attachment in situ in the body. For example, keels, suture anchors, bone anchors, mesh or other bone attachment material, and the like.

Thus, the disc replacement can be manufactured to the shape of the patient's treated intervertebral disc (IVD), specifically in term of cross section geometry and area, and 3-D surfaces (concavity) defined by the superior and inferior adjacent vertebral endplates, while restoring an appropriate height and wedge angle for the treated disc space(s). The appropriate thickness and wedge angle may be defined by analyzing the dimensions and geometry of the healthy levels of the patient's lumbar spine and by incorporating this data into predefined algorithms in order to restore an appropriate curve of the spinal lordosis or respond to other specific needs (see FIGS. 6C and 7C discussed below).

Figure 3:
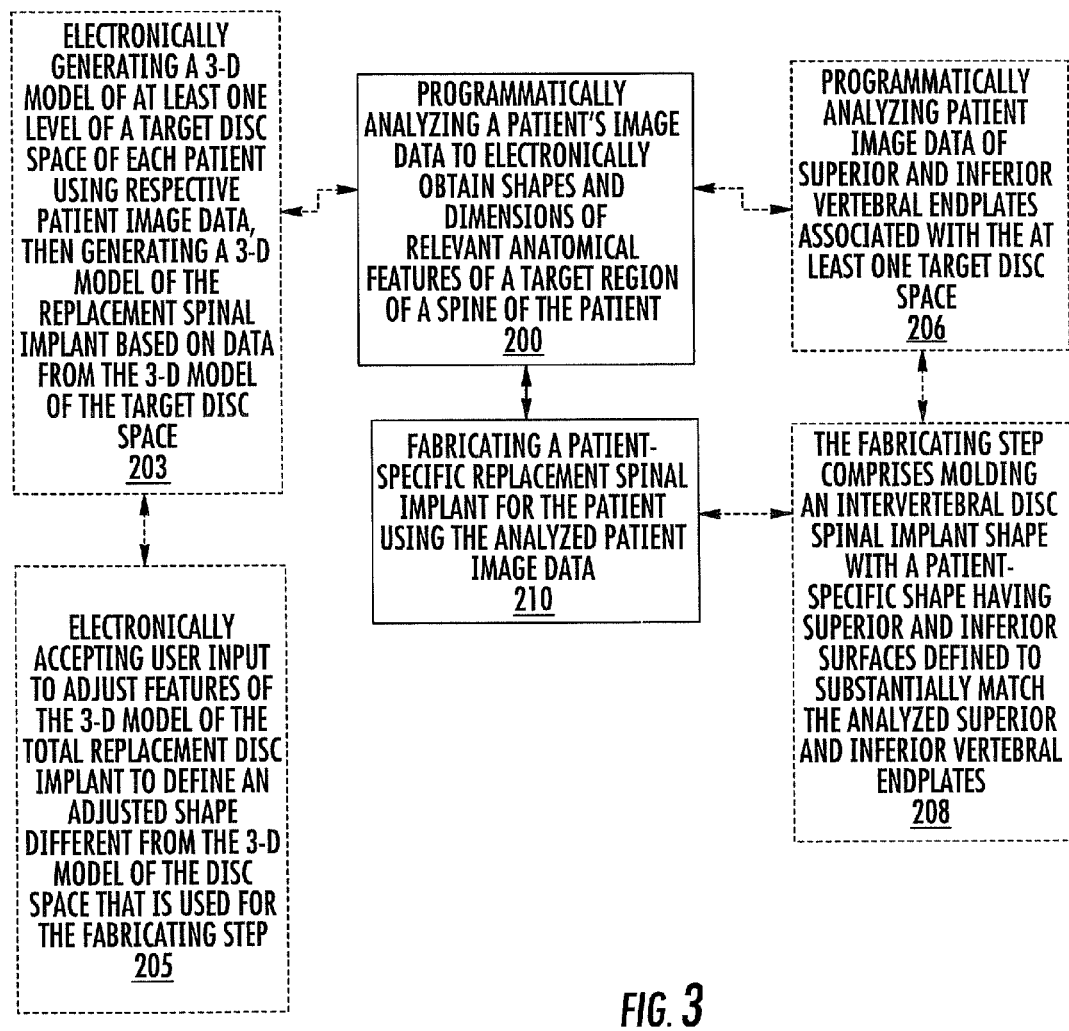
FIG. 3 is a flow chart of operations that can be used to carry out embodiments of the present invention.

FIG. 3 illustrates operations or actions that can be carried out to generate custom spinal implants according to embodiments of the present invention. As shown, a patient's image data can be programmatically analyzed to electronically obtain shapes and dimensions of relevant anatomical features of a target region of a spine of the patient (block 200). A patient-specific replacement spinal implant can be fabricated for the patient using the analyzed patient image data (block 210).

In some embodiments, the spinal implant comprises at least one total disc replacement implant and the method further includes, before the fabricating step, electronically generating a 3-D model of at least one level of a target disc space of each patient using respective patient image data, then generating a 3-D model of the total disc replacement spinal implant based on data from the 3-D model of the target disc space (block 203). Optionally, the method can include electronically accepting user input to adjust features of the 3-D model of total replacement disc implant to define an adjusted shape different from the 3-D model of the disc space that is used for the fabricating step (block 205).

The user input can be by freehand (manual) drawing using a finger contact on the screen, a stencil, light beam, or other input tool. Alternatively, or additionally, the user input can include selectable tools, such as electronically assisted line or curve shape-assisted boundary drawing features, including, for example, spline format tools. Manipulation tools that allow the user to move a drawn line or inserted point, adjust the shape or size, zoom, rotate or otherwise manipulate the shape and/or features or boundary lines can be provided as a tool box or menu selection. An "undo", erase or backtrack tool can be provided to allow ease of editing the initial or altered shape.

In some embodiments, the programmatically analyzing step can include analyzing patient image data of superior and inferior vertebral endplates associated with the at least one target disc space (block 206). The fabricating step can include molding an intervertebral disc spinal implant shape with a patient-specific shape having superior and inferior surfaces defined to substantially match the analyzed superior and inferior vertebral endplates (block 208).

In contrast with conventional disc replacements (and other devices) that can induce stress concentration and potential damage to the bony structures, some embodiments of the present invention can provide 3-D surfaces that substantially, if not exactly, match the irregularities of the bone. Therefore, the contact area between the implant and the local bone structures can be optimized (increased) and the load distribution improved for increased durability of the implant as well as the bone. Also, having matching surfaces at the interfaces with the bone may provide the implant with a more natural/stable position, compared to a similar device with non-matching/standard surfaces. The fixation of the device in situ may also be improved.

Figure 4:
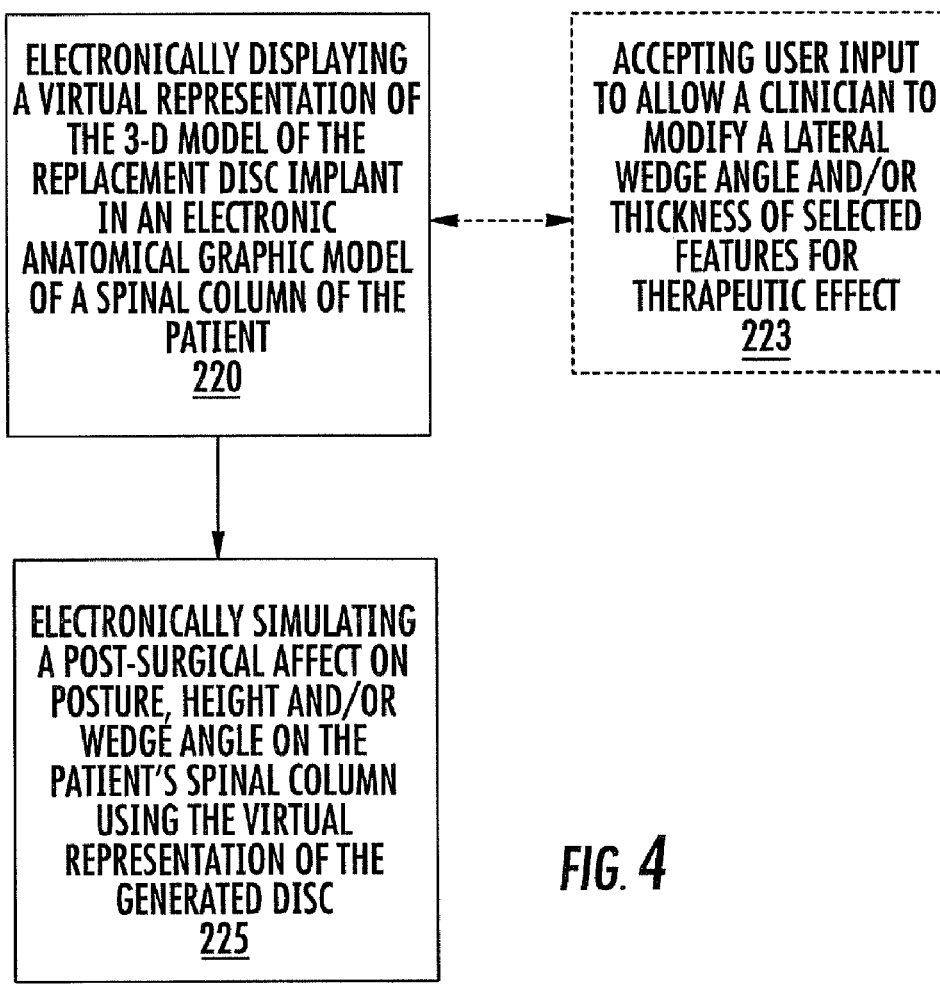
FIG. 4 is a flow chart of other operations that can be used to carry out embodiments of the present invention.

FIG. 4 illustrates exemplary operations that can be carried out according to some embodiments of the present invention. As shown, a virtual representation of the 3-D model of the replacement disc implant can be electronically displayed in an electronic anatomical graphic model of a spinal column of the patient (block 220). The method can then electronically graphically simulate a post-surgical affect on posture, height and/or wedge angle on the patient's spinal column using the virtual representation of the generated disc (block 225).

In some embodiments, the simulating can include accepting user input to allow a clinician to modify a lateral wedge angle and/or thickness or other selected features for therapeutic effect (block 223). In some embodiments, geometry and features of the implant may be changed or adjusted according to the needs of the patient and/or according to the needs of the physician in order to customize the treatment and/or improve the ease of implantation of the device. For example, the implant device could be changed to match a specific approach, be usable with various additional means of fixation and also relocate the attachment points, if applicable.

Concerning disc replacements, embodiments of the invention may find applications for patients with degenerative disc diseases, as well as for patients with scoliosis, on one or several levels. In some embodiments, an implant could be made with a lateral wedge angle to comply with a scoliotic level or potentially compensate for lateral inclination of the disc space.

An exemplary custom construct process cycle may include:
1. Take scans (CT or MR) of the patient's (whole) lumbar spine
   Take appropriate measurements, specifically:
      Healthy discs dimensions
      Vertebrae dimensions
      Level of degeneration of the level(s) to be treated (dimensions)
2. Make a 3-D reconstruction of the patient's lumbar spine
3. From the 3-D reconstruction of the lumbar spine, export the 3-D surfaces of the vertebral endplates of the level(s) to be treated into CAD software
4. Compute thickness and wedge angle to be restored from the available measured data (using appropriate algorithms)
5. Using the CAD software, build the 3-D model of the TDR to be implanted
   Use 3-D endplate surfaces
   Use computed dimensions (thickness and wedge angle and others if applicable)
   Incorporate any other custom features to the model (from physician inputs and to customize treatment)
   Potentially, make several custom parts available (for example, in more than one thickness or with different bone attachment configurations to provide alternate configurations that may be used at implantation)
6. Make adjustment in the manufacturing materials to be able to produce the part(s)
7. Produce custom device(s)

In some embodiments, data taken from the medical images (i.e., CT and/or MRI scans) is used to generate a 3D model of the bone strictures of the considered level(s). Conventional software such as MIMICS from Materialise, (having a place of business in Ann Arbor, Mich.) can be used to form the 3D spinal implant model.

The geometry of a target degenerated disc space can be obtained by a relatively simple subtraction of 3D parts. For example, an approximate or rough 3D shape can be electronically generated that covers the target disc space. The volume of the vertebral bodies can be subtracted from this shape to obtain the 3D implant model that has the volume and geometry of the disc space, with the 3D surfaces of the endplates. The implant geometry can be done using MIMICS or another CAD software, such as SolidWorks, from SolidWorks, Corporation, Concord, Mass. The 3D model of the degenerated disc space can then be exported in the desired CAD module.

After being exported in a CAD module, the geometry/ geometric features of the implant model of the degenerated disc space can be changed or adjusted as desired or needed. This can be done with a trained operator using CAD software. However, embodiments of the invention can provide modules or software that can apply standard changes (thickness, wedge angles, diameter, contour, attachment features, partition of the artificial disc for composite TDR, and the like) that could be used directly by physicians and be accessible on a workstation 25 (FIG. 1A).

Some embodiments of the invention can accept clinician input such as "Add 2 mm of thickness to the disc" as a physician request that is clearly defined and that can be processed to change the 3D model of the custom disc. However, if a request from a physician cannot be directly quantified, such as "the device should not apply or apply limited stress the right postero-lateral section of the upper endplate as there is potential of a fracture in this area", then the systems of the present invention can answer this request by iteratively changing predefined parameters (dimensions/speciific features of the disc—a simple example for this case could be to create a recess in the designated area or have a softer material in contact with it) and simulate the custom disc through a custom finite element model of the patient's treated functional spine unit. The finite element model can be built from the 3D model of the bone structures that would be meshed and exported into FEM software such as ABAQUS or ANSYS. The system can be configured to define suitable material properties, interfaces, simulation of surrounding tissues, and different types of physiological simulations based on different implant and patient configurations. Additional data can be used to allow adjustments, even very subtle adjustments on the implant geometry and material properties, which can also be customized. These types of adjustments may improve the range of indications and success rate of TDRs and many other devices.

Once the 3D model of the custom device is complete (either done by the physician directly or by the manufacturer according to predefined requirements), the model can be used to produce the components (such as molds) that will be used for the manufacturing of the custom part (see FIGS. 11A-11D, 12A-12C).

In some embodiments, the custom implant 75 can be a three-dimensional TDR spinal disc implant structure that provides a desired anatomical shape, shock absorbency and mechanical support. In some embodiments, the anatomical shape can have an irregular solid volume to fill a target intervertebral disc space. The coordinates of the implant body can be described using the anatomic directions of superior (toward the head), inferior (toward the feet), lateral (away from the midline), medial (toward the midline), posterior (toward the back), and anterior (toward the front). From a superior view, the implanted device has a kidney shape with the hilum toward the posterior direction. The margins of the device in sagittal section are generally contained within the vertebral column dimensions. The term "primary surface" refers to one of the superior or inferior (endplate) surfaces. The size of the prosthetic spinal disc 75 will typically vary for different individuals. A typical "average" size of an adult lumbar disc is 3-5 cm in the minor axis, 5 cm in the major axis, and 1.5 cm in thickness, but each of these dimensions can vary.

Figures 6A, 6B, 6C:
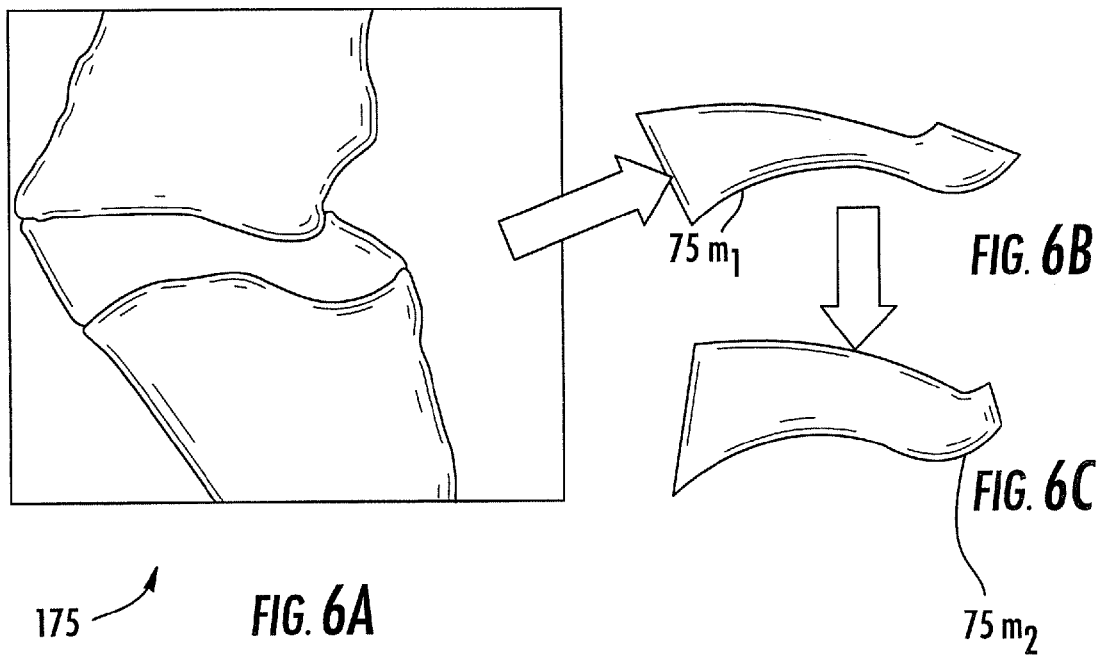
FIG. 6A is a 2-D screen shot of a patient image of a spinal disc space targeted for treatment.
FIG. 6B is an electronic model of a natural spinal disc constructed to have substantially the same dimensions and shape as the spinal disc in the image of FIG. 6A.
FIG. 6C is an electronic model of spinal implant adjusted in thickness and wedge angle relative to the natural disc model shown in FIG. 6B to reduce spondylolisthesis according to embodiments of the present invention.

FIGS. 5A-5C and 6A-6C illustrate in 2-D an exemplary construct process as described above. As shown in FIGS. 5A and 6A, in a first step, image data of the patient's spine 175 can be electronically obtained and analyzed and the shape of the vertebral endplates can be identified. FIGS. 5B and 6B show that in a second step, a 3-D model of the disc space (generically referred to by designation 75$m$) can be created. FIGS. 5C and 6C illustrate that a first disc model 75$m_1$ can be adjusted or corrected according to the patient's pathology to provide the custom implant shape 75$m_2$. Thus, the corrected model 75$m_2$ can define the shape of the custom designed total disc replacement. FIGS. 5A-5C illustrate a custom disc corrected for scoliotic angle and FIGS. 6A-6C illustrate a custom disc corrected for reduction of spondylolisthesis and increase of thickness and wedge angle.

Figure 7:
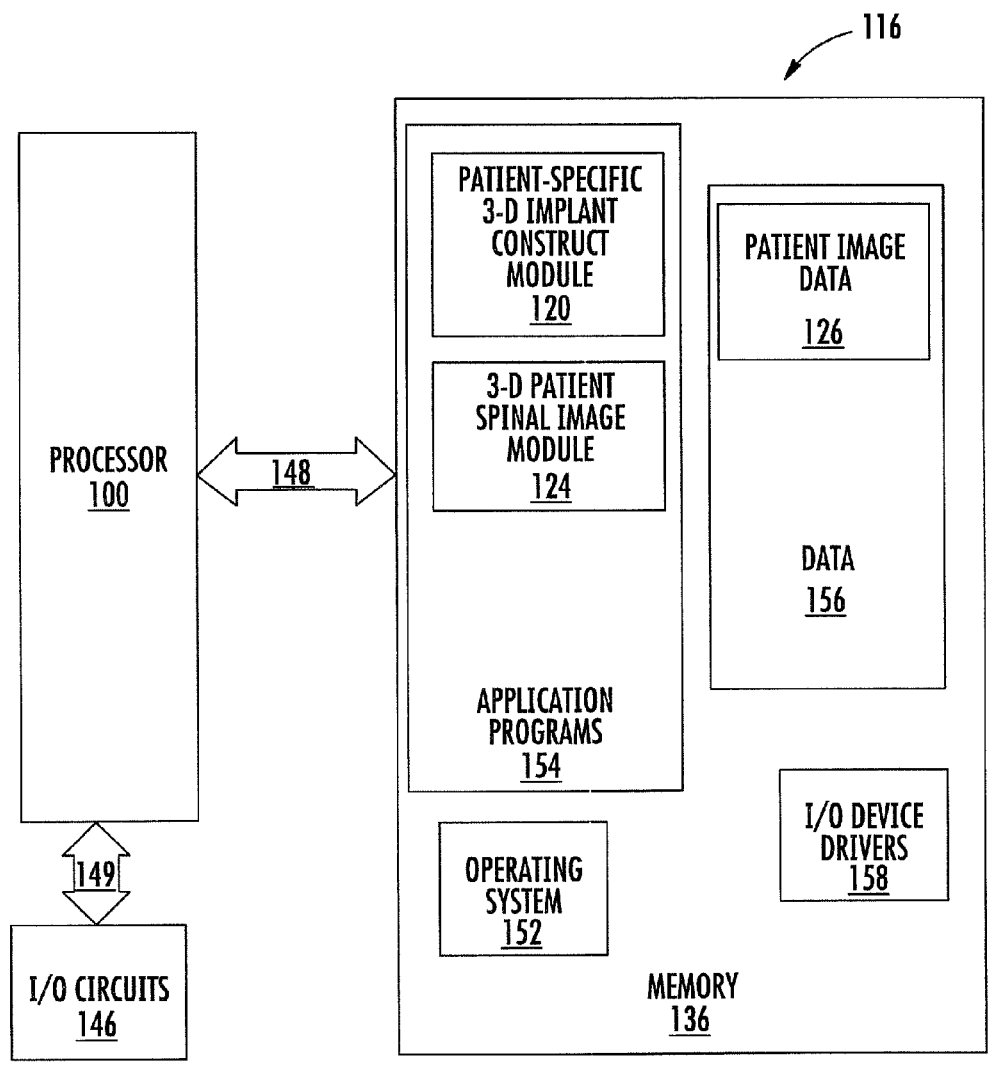
FIG. 7 is a block diagram of a data processing system according to embodiments of the present invention.

Referring now to FIG. 7, a data processing system 116 that may be used to implement the custom system described herein and/or shown in the figures, in accordance with some embodiments of the present invention, comprises input device(s) 25 (FIG. 1A) which can include a keyboard or keypad, a display 25d (FIG. 1A), and a memory 136 that communicate with a processor 100. The data processing system 116 may further include an input/output (I/O) circuits and/or data port(s) 146 that also communicate with the processor 100. The system 116 may include removable and/or fixed media, such as floppy disks, ZIP drives, hard disks, or the like, as well as virtual storage, such as a RAMDISK. The I/O data port(s) 146 may be used to transfer information between the data processing system 116 and another computer system or a network (e.g., the Internet). These components may be conventional components, such as those used in many conventional computing devices, and their functionality, with respect to conventional operations, and is generally known to those skilled in the art.

The processor 100 may be, for example, a commercially available or custom microprocessor. The memory 136 is representative of the one or more memory devices containing the software and data used for providing a calendar based time limited passcode system with interface on a display in accordance with some embodiments of the present invention. The memory 136 may include, but is not limited to, the following types of devices: cache, ROM, PROM, EPROM, EEPROM, flash, SRAM, and DRAM.

As shown in FIG. 7, the memory 136 may contain up to two or more categories of software and/or data: an operating system 152, I/O Device Drivers 158, data 156 such as Patient Image Data 126, and application programs 154.

As will be appreciated by those of skill in the art, the operating system 152 may be any operating system suitable for use with a data processing system, such as IBM®, OS/2®, AIX® or zOS® operating systems or Microsoft® Windows®95, Windows98, Windows2000 or WindowsXP operating systems Unix or Linux™. IBM, OS/2, AIX and zOS are trademarks of International Business Machines Corporation in the United States, other countries, or both while Linux is a trademark of Linus Torvalds in the United States, other countries, or both. Microsoft and Windows are trademarks of Microsoft Corporation in the United States, other countries, or both. The input/output device drivers 158 typically include software routines accessed through the operating system 152 by the application programs 154 to communicate with devices such as the input/output circuits 146 and certain memory 136 components. The application programs 154 are illustrative of the programs that implement the various features of the circuits and modules according to some embodiments of the present invention. Finally, the data 156 represents the static and dynamic data used by the application programs 154 the operating system 152 the input/output device drivers 158 and other software programs that may reside in the memory 136.

As further illustrated in FIG. 7, according to some embodiments of the present invention, application programs 154 may include a Patient-Specific 3-D Implant Construct Module 120 and may optionally include a 3-D Patient Spinal Image Module 124 that can simulate a post-surgical spinal configuration interactively using custom implants electronically inserted in the spine. The application program 154 may be located in a local server (or processor) and/or database or a remote server (or processor) and/or database, or combinations of local and remote databases and/or servers.

While the present invention is illustrated with reference to the application programs 154, 120, 124 in FIG. 7, as will be appreciated by those of skill in the art, other configurations fall within the scope of the present invention. For example, rather than being application programs 154 these circuits and modules may also be incorporated into the operating system 152 or other such logical division of the data processing system. Furthermore, while the application program 154 is illustrated in a single data processing system, as will be appreciated by those of skill in the art, such functionality may be distributed across one or more data processing systems in, for example, the type of client/server arrangement described above. Thus, the present invention should not be construed as limited to the configurations illustrated in FIG. 7 but may be provided by other arrangements and/or divisions of functions between data processing systems. For example, although FIG. 7 is illustrated as having various circuits and modules, one or more of these circuits or modules may be combined or separated without departing from the scope of the present invention.

Although FIG. 7 illustrates exemplary hardware/software architectures that may be used in systems such as shown in FIGS. 1A-1B, 2-4, and 8-9, it will be understood that the present invention is not limited to such a configuration but is intended to encompass any configuration capable of carrying out operations described herein. Moreover, the functionality of the data processing systems and the hardware/software architectures may be implemented as a single processor system, a multi-processor system, or even a network of stand-alone computer systems, in accordance with various embodiments of the present invention.

Computer program code for carrying out operations of data processing systems discussed above with respect to the figures may be written in a high-level programming language, such as Java, C, and/or C++, for development convenience. In addition, computer program code for carrying out operations of embodiments of the present invention may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller.

Figure 8:
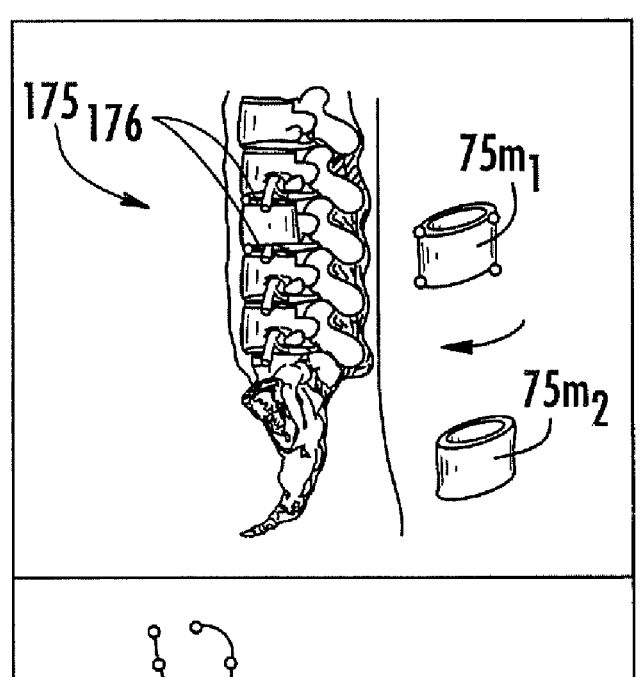
FIG. 8 is a schematic illustration of an interactive workstation configured to generate a model of a spinal implant and allow electronic alteration of features of the spinal implant according to embodiments of the present invention.
Figure 9:
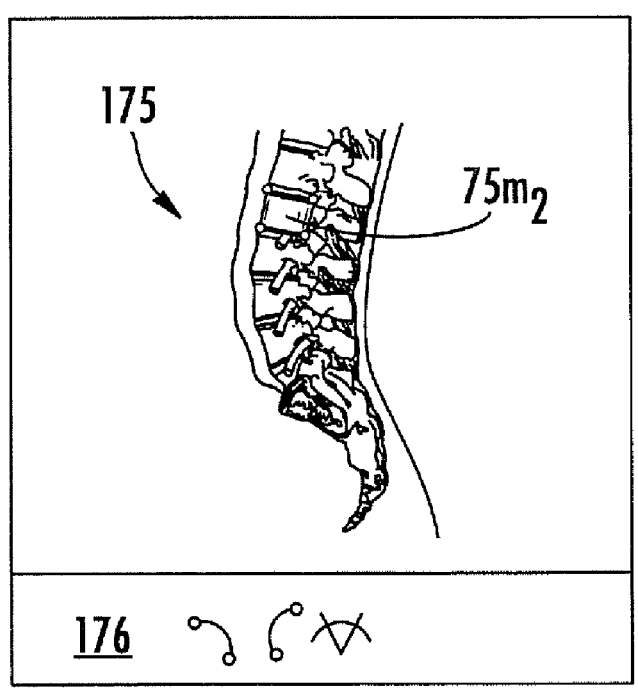
FIG. 9 is a schematic illustration of a workstation configured to simulate a patient's lumbar spine and illustrate projected therapeutic effect on spinal configuration/posture using an electronic model of a spinal implant.

FIG. 8 is a schematic illustration of an interactive display 25d. As shown, a clinician can select computer-assisted tools 176 that can be electronically placed or overlayed onto the patient image 175 to select the target region of interest for implant construct, excision review (and relevant endplates). A first model $75m_1$ can be electronically constructed. A clinician can rotate, turn or otherwise turn the disc to illustrate views of the 3-D disc model $75m_1$. The interactive display 25d can also allow the clinician to alter the shape of one or more features of the disc $75m_1$ to generate an adjusted model $75m_2$. FIG. 9 illustrates a simulated projected post-surgical patient spine configuration using the patient image data and either disc model $75m_1$ or $75m_2$. The system can be configured to suggest implant configurations based on measurements of the patient data and a desired treatment outcome. The simulated spine (entire vertebral column or subsets of the spine) can be generated using patient image data projected onto or based on known commercially available 3-D interactive human anatomy software for medical and heath professionals, such as, for example, *Interactive Spine*, by Hilali Noordeen et al.

Figure 11A:
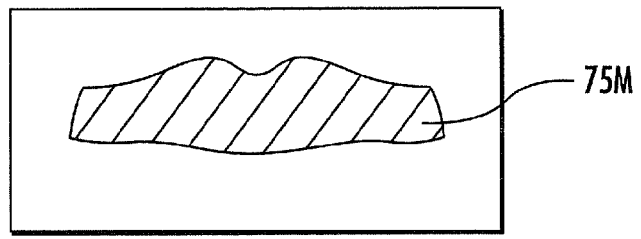
FIGS. 11A-11D are schematic illustrations of exemplary operations that can be used to mold patient-specific spinal implants according to embodiments of the present invention.
Figure 11B:

FIGS. 11A-11D illustrate exemplary operations that can be used to mold patient-specific implants. As shown in FIG. 11A, the 3D model 75*m* of the patient's target treatment region/space is obtained. As shown in FIG. 11B, a substantially rigid "master" mold 77 can be fabricated based on data from the 3D model. The master mold may comprise a metallic, typically stainless steel body that may be machined. In some embodiments, the master mold can be elastomeric (and may be 3D printed).

In some embodiments, the shape of the master mold is substantially the same as the 3D model 75*m* but dimensions of the master mold 77 may be smaller/reduced compared to the end replacement implant body to compensate for the increase in volume of the part during processing. For example, for PVA hydrogel implants, the volume of the implant can increase before implantation due to hydration of the hydrogel, in order to have final dimensions that meet the 3-D implant shape requirements.

Figure 11C:
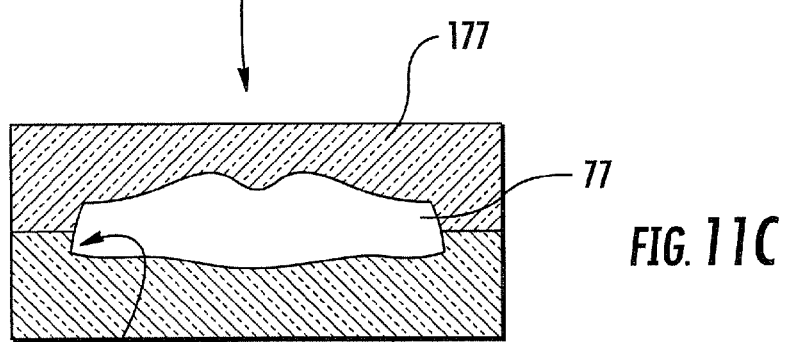
Figure 11D:
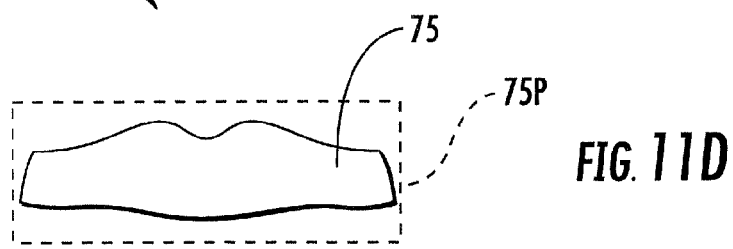

As shown in FIG. 11C, an insert/mold 177 is formed about the master and produced using the master 77. Silicone may be used to form the mold 177. Silicone may be a suitable economical material for a disposable mold. As shown in FIG. 11C, the mold 77 has a cavity 177*c* that has the shape of the master 77 used to shape the implant to be manufactured. The mold 177 can then be used to produce the implant 75 (FIG. 11D). The molding process can be any suitable process, such as for example, an injection molding process, as well as processes described in co-ending U.S. Provisional Application Ser. No. 60/761,903, the contents of which are hereby incorporated by reference as if recited in full herein. In some embodiments, a silicone or other elastomeric insert can be placed into a metallic frame to define the cavity shape and size instead of having the cavity defined by the metallic frame itself. Also, the flexibility of an elastomeric mold, such as for example, silicone, can allow for some variation of the mold cavity during heating and cooling periods (if applicable). As shown in FIG. 11D, the implant 75 can be placed in a sterile package 75 and otherwise processed (trimmed (if applicable), thermally cycled, hydrated, packaged, sterilized (one or more of the operations can be carried out before packaging) and finalized for use.

FIGS. 12A-12C illustrate another methodology that can be used to form the custom implant. As shown in FIG. 12A, similar to FIG. 11A, the 3-D model 75*m* can be obtained. A rigid mold 178 comprising a plurality of attachable members 178$_1$, 178$_2$, 178$_3$, 178$_4$ can be fabricated, such as machined, based on data from the 3D model 75*m* with inner surfaces shaped (3D surfacing) in order to create, when assembled, a cavity 178*c* with the shape of the implant 75 to be produced. The mold body typically includes two or more attachable members although shown with four discrete members that are held together with frame members 179$_1$, 179$_2$. Pins, screws, clamps or other mechanisms can be used to hold the mold members 178$_1$, 178$_2$, 178$_3$, 178$_4$ snugly together during the molding process. In some embodiments, the mold cavity 178*c* is adjusted to have a different size from that of the 3-D model 75*m* (smaller) so that the implant 75 will have the required dimensions after swelling through processing, such as, for hydrogels, a hydration process.

As before, the mold 178 can be used to produce the implant 75. The molding can be carried out using an injection molding process as well as the process described in the above-referenced provisional application. The molding system can be configured to allow for variation of the volume of the mold cavity 178*c* during heating and cooling periods, such as holding the members together using a spring system or a hydraulic/pneumatic control of the pressure inside the mold cavity 178*c* through relative controlled displacement of the different mold components 178$_1$, 178$_2$, 178$_3$, 178$_4$. As before, the implant can be placed in a sterile package 75*p*. The implant can be processed to meet size and functional requirements before or after packaging (i.e., trimmed (if applicable), thermally cycled, hydrated, packaged, sterilized) and finalized.

The flowcharts and diagrams of FIGS. 1-12 illustrate the architecture, functionality, and operations of some embodiments of methods, systems, and/or computer program products for providing custom implants. In this regard, each block represents a module, segment, or portion of code, which comprises one or more executable instructions for implementing the specified logical function(s). It should also be noted that in other implementations, the function(s) noted in the blocks might occur out of the order noted. For example, two blocks shown in succession may, in fact, be executed substantially concurrently or the blocks may sometimes be executed in the reverse order, depending on the functionality involved.

In some embodiments, the implant 75 can be configured as a flexible elastomeric MRI and CT compatible (i.e., compatible for use in CT and MRI imaging apparatus) spinal intervertebral disc implant. The implant 75 can have a solid elastomeric body with mechanical compressive and/or tensile elasticity that is typically less than about 100 MPa (and typically greater than 1 MPa), with an ultimate strength in tension generally greater than about 100 kPa, that can exhibit the flexibility to allow at least 2 degrees of rotation between the top and bottom faces with torsions greater than 0.01 N-m without failing. The implant 75 can be configured to withstand a compressive load greater than about 1 MPa.

The implant 75 can include bone attachment material that is typically between about 0.25 mm to about 20 mm thick, and is more typically between about 0.5 mm to about 5 mm thick. In some embodiments, the mesh comprises a DACRON mesh of about 0.7 mm thick available as Fablok Mills Mesh #9464 from Fablok Mills, Inc., located in Murray Hill, N.J. The mesh may comprise cryogel material to increase rigidity.

The implant 75 can be made from any suitable elastomer capable of providing the desired shape, elasticity, biocompatibility, and strength parameters. The implant 75 can be configured with a single, uniform average durometer material and/or may have non-linear elasticity (i.e., it is not constant). The implant 75 may optionally be configured with a plurality of durometers, such as a dual durometer implant. The implant 75 can be configured to be stiffer in the middle, or stiffer on the outside perimeter. In some embodiments, the implant 75 can be configured to have a continuous stiffness change, instead of two distinct durometers. A lower durometer corresponds to a lower stiffness than the higher durometer area. For example, one region may have a compressive modulus that is between about 11-100 MPa, while the other region may have a compressive modulus that is between 1-10 MPa.

The implant 75 can have a tangent modulus of elasticity that is about 1-10 MPa, typically about 3-5 MPa, and water content of between about 30-60%, typically about 50%.

Some embodiments of the implantable spinal disc 75 can comprise polyurethane, silicone, hydrogels, collagens, hyalurons, proteins and other synthetic polymers that are configured to have a desired range of elastomeric mechanical properties, such as a suitable compressive elastic stiffness and/or elastic modulus. Elastomers useful in the practice of the invention include polyvinyl alcohol (PVA) hydrogels, polyvinyl pyrrolidone, poly HEMA, HYPAN™ and Salubria® biomaterial. Methods for preparation of these polymers and copolymers are well known to the art. Examples of known processes for fabricating elastomeric cryogel material is described in U.S. Pat. Nos. 5,981,826 and 6,231,605, the contents of which are hereby incorporated by reference. See also, Peppas, Poly (vinyl alcohol) hydrogels prepared by freezing—thawing cyclic processing. Polymer, v. 33, pp. 3932-3936 (1992); Shauna R. Stauffer and Nikolaos A. Peppas.

Polymers such as silicone and polyurethane are generally known to have (compressive strength) elastic modulus values of less than 100 MPa. Hydrogels and collagens can also be made with compressive elasticity values less than 20 MPa and greater than 1.0 MPa. Silicone, polyurethane and some cryogels typically have an ultimate tensile strength greater than about 100 or 200 kiloPascals. Materials of this type can typically withstand torsions greater than 0.01 N-m without failing.

Figure 10:
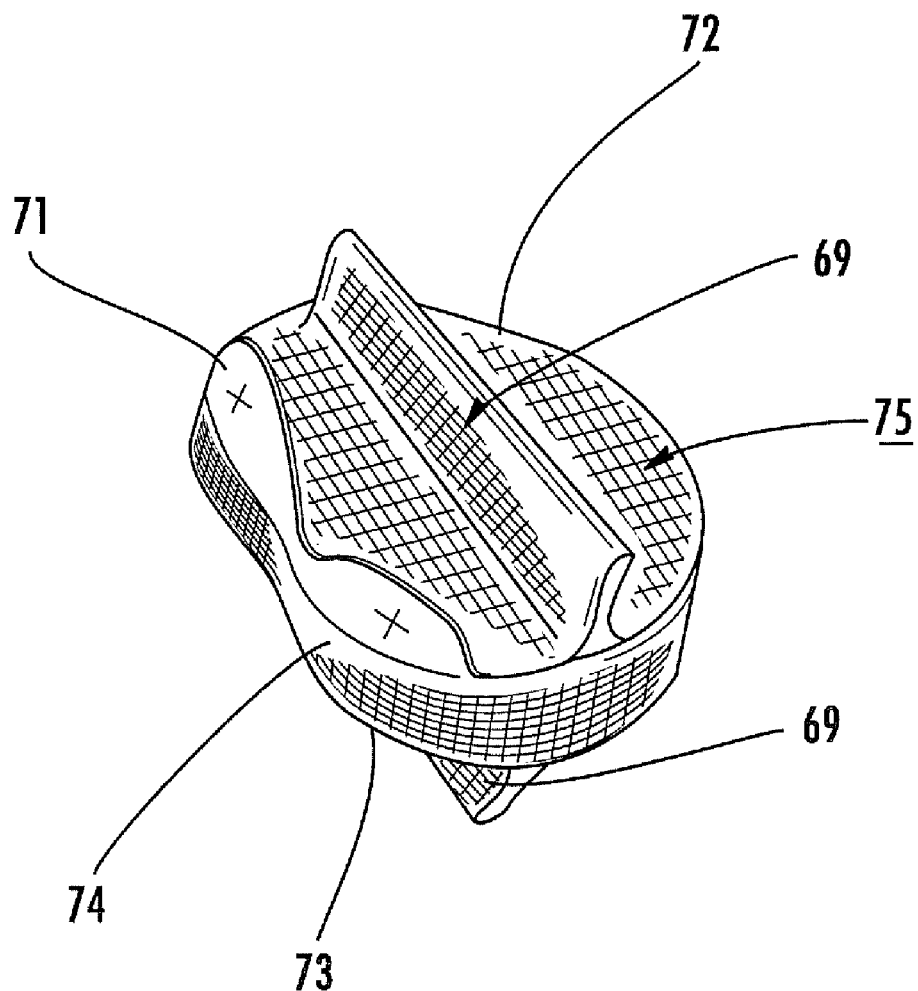
FIG. 10 is a top perspective view of a custom TDR implant according to some embodiments of the present invention.

As shown in FIG. 10, the spinal disc body 75 may have a circumferential surface 74, a superior surface 72, and an inferior surface 73. The superior and inferior surfaces 72, 73, respectively, may be substantially convex, and may be configured with the same surface configuration of the natural disc, to mate with concave vertebral bones adjacent thereto. One or more of the surfaces may also be substantially planar or concave. The circumferential surface 74 of spinal disc body 75 corresponds to the annulus fibrosis ("annulus") of the natural disc and can be described as the annulus surface 74. The superior surface 72 and the inferior surface 73 of spinal disc body 75 correspond to vertebral end plates ("end plates") in the natural disc. The medial interior of spinal disc body 75 corresponds to the nucleus pulposus ("nucleus") of the natural disc.

The implant 75 can include a porous covering, typically a mesh material layer, on each of the superior and inferior primary surfaces 72, 73, respectively, and may also include a porous, typically mesh, material layer on the annulus surface 74 (not shown). Bone attachment members can engage the mesh material at defined locations 71 noted by the "cross" in FIG. 10. The implant 75 can include flex or rigid keels 69 on the superior and inferior surfaces as shown.

The implant 75 may be configured to allow vertical passive expansion or growth of between about 1-40% in situ as the implant 75 absorbs or intakes liquid due to the presence of body fluids. The passive growth can be measured outside the body by placing an implant in saline at room temperature and pressure for 5-7 days, while held in a simulated spinal column in an intervertebrate space between two simulated vertebrates. It is noted that the passive expansion can vary depending, for example, on the type of covering or mesh employed and the implant material. For example, in some embodiments, the mesh coverings along with a weight percentage of (PVA) used to form the implant body are configured to have between about 1-5% expansion in situ.

In addition, in some embodiments, the mesh may comprise a biocompatible coating or additional material on an outer and/or inner surface that can increase the stiffiess. The stiffening coating or material can include PVA cryogel.

In some embodiments, the implant body 75 is a substantially solid crystalline PVA hydrogel having a unitary body shaped to substantially correspond to a natural spinal disc of the patient. An exemplary hydrogel suitable for forming a spinal implant is (highly) hydrolyzed crystalline poly (vinyl alcohol) (PVA). PVA cryogels may be prepared from commercially available PVA material, typically comprising powder, crystals or pellets, by any suitable methods known to those of skill in the art. Other materials may also be used, depending, for example, on the application and desired functionality. Additional reinforcing materials or coverings, radiopaque markers, calcium salt or other materials or components can be molded on and/or into the molded body. Alternatively, the implant can consist essentially of the molded PVA body.

The moldable primary implant material can be placed in a mold. The moldable material comprises an irrigant and/or solvent and about 20 to 70% (by weight) PVA powder crystals. The PVA powder crystals can have a MW of between about 124,000 to about 165,000, with about a 99.3-100% hydrolysis. The irrigant or solvent can be a solution of about 0.9% sodium chloride. The PVA crystals can be placed in the mold before the irrigant (no pre-mixing is required). The mold has the desired 3-D implant body shape. A lid can be used to close the mold. The closed mold can be evacuated or otherwise processed to remove air bubbles from the interior cavity. For example, the irrigant can be overfilled such that, when the lid is placed on (clamped or secured to) the mold, the excess liquid is forced out thereby removing air bubbles. In other embodiments, a vacuum can be in fluid communication with the mold cavity to lower the pressure in the chamber and remove the air bubbles. The PVA crystals and irrigant can be mixed once in the mold before and/or after the lid is closed. Alternatively, the mixing can occur naturally without active mechanical action during the heating process.

Typically, the mold with the moldable material is heated to a temperature of between about 80° C. to about 200° C. for a time sufficient to form a solid molded body. The temperature of the mold can be measured on an external surface. The mold can be heated to at least about 80-200° C. for at least about 5 minutes and less than about 8 hours, typically between about 10 minutes to about 4 hours. The (average or max and min) temperature can be measured in several external mold locations. The mold can also be placed in an oven and held in the oven for a desired time at a temperature sufficient to bring the mold and the moldable material to suitable temperatures. In some embodiments, the mold(s) can be held in an oven at about 100-200° C. for about 2-6 hours; the higher range may be used when several molds are placed therein, but different times and temperatures may be used depending on the heat source, such as the oven, the oven temperature, the configuration of the mold, and the number of items being heated.

Liners can be placed in the mold to integrally attach to the molded implant body during the molding process. In some embodiments, osteoconductive material, such as, for example, calcium salt can be placed on the inner or outer surfaces of the covering layers and/or the inner mold surfaces (wall, ceiling, floor) to coat and/or impregnate the mesh material to provide osteoconductive, tissue-growth promoting coatings.

After heating, the implant body can be cooled passively or actively and/or frozen and thawed a plurality of times until a solid crystalline implant is formed with the desired mechanical properties. The molded implant body can be removed from the mold prior to the freezing and thawing or the freezing and thawing can be carried out with the implant in the mold. Alternatively, some of the freeze and thaw steps (such as, but not limited to, between about 0-10 cycles) can be carried out while the implant is in the mold, then others (such as, but not limited to, between about 5-20 cycles) can be carried out with the implant out of the mold.

Before, during and/or after freezing and thawing (but typically after demolding), the molded implant can be placed in water or saline (or both or, in some embodiments, neither). The device can be partially or completely dehydrated for implantation. The resulting prosthesis can have an elastic modulus of at least about 2 MPa and a mechanical ultimate strength in tension and compression of at least 1 MPa, preferably about 10 MPa, and under about 100 MPa. The prosthesis may allow for between about 1-10 degrees of rotation between the top and bottom faces with torsions of at least about 1 N-m without failing. The implant can be a single solid elastomeric material that is biocompatible by cytotoxicity and sensitivity testing specified by ISO (ISO 10993-5 1999: Biological evaluation of medical devices—Part 5: Tests for in vitro cytotoxicity and ISO 10993-10 2002: Biological Evaluation of medical devices—Part 10: Tests for irritation and delayed-type hypersensitivity).

Figure 13:
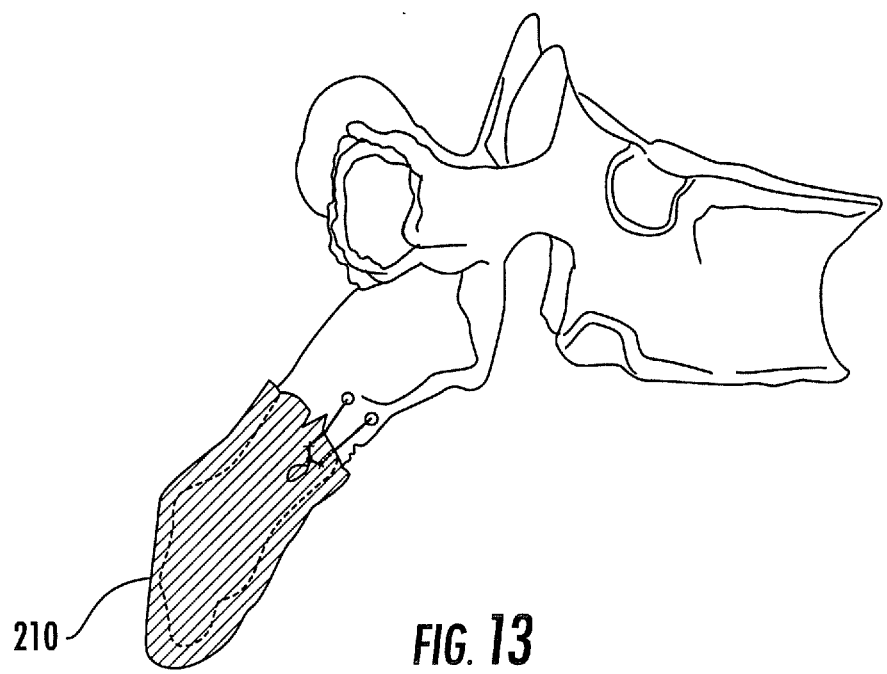
FIG. 13 is a side view of an exemplary custom spinous process cuff according to some embodiments of the present invention.
Figure 14:
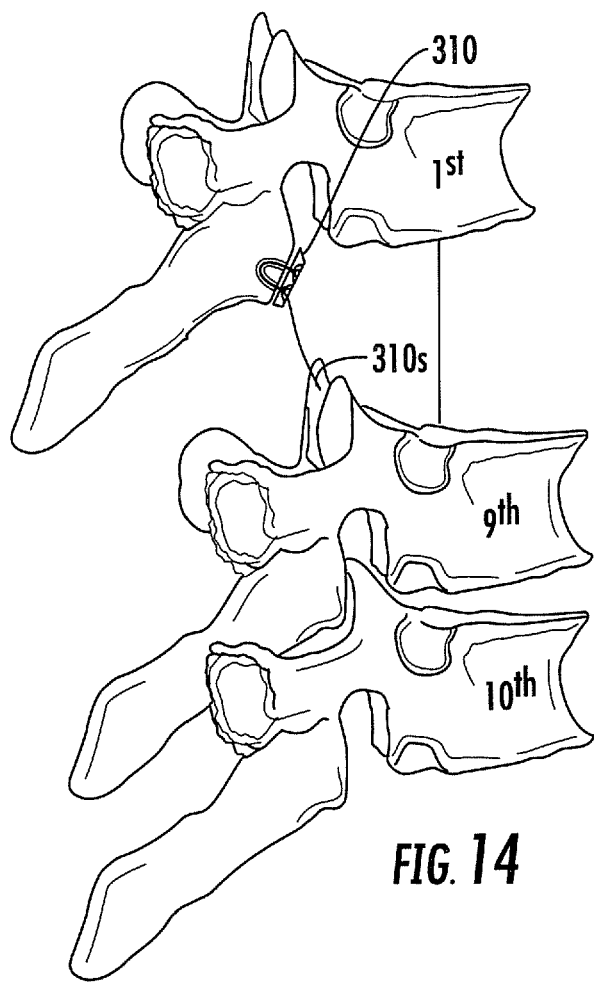
FIG. 14 is a side view of a spine illustrating a custom wide range facet prosthesis according to some embodiments of the present invention.

The testing parameters used to evaluate the compressive tangential modulus of a material specimen can include:
Test type: unconfined compression
Fixtures: flat platens, at least 30 mm diameter
Rate: 25.4 mm/sec to 40% strain
Temperature: room temp (~22° C.)
Bath: samples stored in saline or water until immediately before test
Samples: cylinders, 9.8±0.1 mm height, 9.05±0.03 mm diameter
Compressive Tangential Modulus calculated at 15, 20, and 35% strain FIG. 13 illustrates a custom spinous process implant 210 that can be fabricated to have patient-specific shapes and/or sizes and FIG. 14 illustrates a patient-specific synthetic wide range facet implant 310 in position in the spine. The implant 310 is configured as a "spinal facet joint". This term refers to the location at which vertebral bodies meet at a rear portion of the spine. The shape of facet joints change along the length of the spine. The facet joint includes bone, cartilage, synovial tissue, and menisci. The implant 310 can be an elastic body that is configured to substantially conformably reside on an outer surface of the bone in a manner that allows a relatively wide range of motion between the bones forming the joint. The implants 310 and 210 can be substantially "conformal" so as to have sufficient flexibility to substantially conform to a target structure's shape. The facet implant or prosthesis 310 can be applied to one surface 310s (one side) of the facet joint (the bone is resurfaced by the implant) or to both surfaces of the joint, and/or may reside therebetween as a spacer to compress in response to loads introduced by the cooperating bones at the facet joint and still allow motion therebetween. The spinal facet joint implant 310 can be configured to provide "wide range motion"; this phrase refers to the substantially natural motion of the bones in the facet joint which typically include all ranges of motion (torsion, lateral and vertical). The implant 310 can have a thickness that is less than about 6 mm, typically between about 0.001-3 mm, and may be between about 0.01 mm to about 0.5 mm. The target structure's shape can be either the upper portion of the lower bone or the lower portion of the upper bone (one of the two vertebral bones) that meet at the rear of the spine.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A method for generating custom implants, comprising:
    programmatically analyzing a patient's image data to electronically obtain shapes and dimensions of relevant anatomical features of a target region of the patient;
    displaying an electronic model of a spinal implant based on the programmatically analyzing step;
    accepting user input to electronically modify the model with a change in at least one of shape, size and material formulation of moldable material for the molded spinal implant; and
    displaying a modified electronic model based on the user input with a corresponding change in anatomical structure in an anatomical model of the patient's spine to thereby allow a user to view potential therapeutic outcomes or affect on a patient using different models of the spinal implant;
    then
    fabricating a patient-specific replacement, non-articulating molded spinal implant for the patient using the analyzed patient image data, wherein the molded spinal implant has a molded custom 3-D bone interface surface that has contours that match excisable natural bone at a contact surface of adjacent local bone of the patient.

2. A method according to claim 1, wherein the programmatically analyzing step comprises analyzing patient image data of superior and inferior vertebral endplates associated with the at least one target disc space, and wherein the fabricating step comprises molding the intervertebral total disc replacement implant with superior and inferior surfaces having the custom 3-D bone interface surface with contours that match excisable bone and engage superior and inferior vertebral endplate surfaces, respectively.

3. A method according to claim 1, wherein the spinal implant comprises at least one total disc replacement implant, the method further comprising programmatically defining a mold configuration for generating a single-use disposable mold to fabricate the patient-specific total disc replacement spinal implant using the analyzed patient image data, and wherein the fabricating step comprises molding the disc replacement spinal implant using the defined mold.

4. A method according to claim 1,
    wherein the spinal implant is a replacement disc, and wherein the displaying the modified electronic model comprises electronically graphically simulating a post-surgical affect on (i) posture, height and -wedge angle or (ii) at least a wedge angle on the patient's spinal column using the model of the spinal implant replacement disc.

5. A method according to claim 4, wherein the simulating comprises accepting user input to allow a clinician to modify at least one of a lateral wedge angle or a thickness of selected features to view changes in therapeutic effect.

6. A method according to claim 1, further comprising:
    electronically determining 3-D surface contours of vertebral endplates at the at least one target disc level to be treated using the patient image data.

7. A method according to claim 1, wherein the programmatically analyzing step comprises:
    obtaining medical image data of a patient's lumbar spine;
    measuring relevant dimensions of at least one healthy intervertebral disc based on the medical image data;
    measuring relevant dimensions of at least one vertebrae based on the medical image data; and
    measuring relevant dimensions of a level of degeneration of at least one intervertebral disc ("IVD") to be treated based on the medical image data.

8. A method according to claim 7, wherein the displaying the electronic model is a model of the patient's lumbar spine generated using the obtained medical image data and measured dimensions.

9. A method according to claim 8, wherein the spinal implant is an IVD implant, and wherein the accepting user input is carried out to electronically adjust the obtained shape, the obtained dimensions or the obtained shape and dimensions of the patient's IVD implant based on a desired therapeutic outcome, wherein the displaying the modified electronic model includes electronically displaying simulations of the anatomical model of the patient's lumbar spine, in response to virtual placement of different IVD implant shapes in the anatomical model.

10. A method according to claim 9, further comprising simulating restoring a desired height and wedge angle of a disc space of the patient based on the adjusted shape and dimensions.

11. A method according to claim 1, wherein the patient-specific implant is an arthroplasty implant comprising an elastomeric body.

12. A method according to claim 1, wherein the implant is a non-articulating elastomeric implant devoid of rigid endplates with a custom moldable material formulation for selected mechanical properties based on the patient to provide locally increased or decreased hardness at a superior or inferior surface of the implant to thereby comply with bone density or bone strength of the patient or bone density and bone strength of the patient.

13. A method according to claim 1, wherein the implant comprises crystalline polyvinylalcohol hydrogel.

14. A method according to claim 1, further comprising, before the fabricating step, accepting clinician input to adjust stiffness and flexibility of the custom molded implant at local bone interface regions, wherein the stiffness and flexibility is defined by a mold material used for the molded implant.

15. A method according to claim 1, further comprising accepting clinician input to define a patient-specific implant configuration with locally softer or more flexible regions relative to other regions in a superior or inferior surface defined by the molded implant to thereby comply with the bone density/strength of the patient at the interface with the implant.

16. A method for generating custom spinal implants, comprising:
programmatically analyzing a patient's image data to electronically obtain shapes and dimensions of relevant anatomical features of a spinal region of the patient;
electronically defining an electronic model of a molded implant using the analysis of the patient image data;
accepting user input to adjust the electronic model of the molded implant including to electronically select different moldable material formulations for the electronic model of the molded implant to define at least one of the following: stiffness, hardness, flexibility, compression, tensile strength, torsional strength, or locally increased or decreased hardness at an inferior or superior surface, to thereby further customize the implant to the patient;
electronically displaying different electronic models of the molded implant, with at least one of (i) different sizes, (ii) different shapes, (iii) different shapes and sizes, or (iv) different material formulations, in an anatomical model of the patient's spine in a manner that shows a change in spine alignment or position based on the different implant models; and
electronically defining a configuration of a single-use custom mold with an enclosed mold cavity shape based on a user selected electronic model of the molded implant.

17. A method according to claim 16, further comprising fabricating a patient-specific replacement non-articulating molded spinal implant for the patient using the custom mold, wherein the implant has molded superior and inferior custom 3-D bone interface surfaces that substantially match surface contours of adjacent local bone of the patient.

18. A method according to claim 16, wherein the implant is a total disc replacement implant, and wherein the electronically displaying step comprises displaying electronic simulations of post-surgical anatomical changes in a patient's spine using the different electronic models of the molded implant.

* * * * *